United States Patent [19]

Shroot et al.

[11] Patent Number: 4,558,069
[45] Date of Patent: Dec. 10, 1985

[54] 1,8-DIHYDROXY-9-ANTHRONES DERIVATIVES SUBSTITUTED IN THE 10-POSITION BY AN UNSATURATED RADICAL USED IN HUMAN MEDICINE

[75] Inventors: Braham Shroot, Antibes; Jean Maignan, Tremblay les Gonesse; Gérard Lang, Epinay sur Seine, all of France

[73] Assignee: Groupement d'Interet Economique dit: Centre International de Recherches Dermatologiques C.I.R.D., Valbonne, France

[21] Appl. No.: 615,734

[22] Filed: May 31, 1984

Related U.S. Application Data

[62] Division of Ser. No. 346,893, Feb. 8, 1982, Pat. No. 4,464,301.

[51] Int. Cl.$^4$ ..................... A61K 31/12; A61K 31/34
[52] U.S. Cl. ..................... 514/473; 514/533; 514/569; 514/545; 514/680; 514/859; 514/863
[58] Field of Search ............... 424/279, 331, 317, 308

[56] References Cited

PUBLICATIONS

*Archiv der Pharmazie*, Schultz et al., Band 310, pp. 776–780, (1977).

Primary Examiner—Leonard Schenkman
Attorney, Agent, or Firm—Wegner & Bretschneider

[57] ABSTRACT 1,8-dihydroxy-9-anthrone derivatives, substituted in the 10-position by an unsaturated radical, are described which have utility as ingredients in human and veterinary pharmaceutical and cosmetic preparations and which are compounds of the structural formula

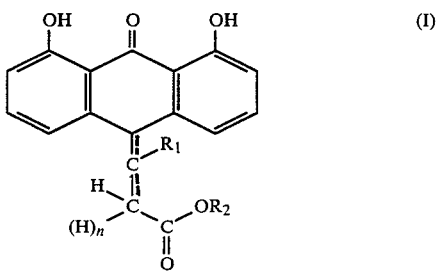

wherein
$R_1$ represents a hydrogen atom or a —$CO_2R'_2$ radical,
$R_2$ and $R'_2$ identical or different, represent a hydrogen atom, a linear or branched chain alkyl radical having 1 to 6 carbon atoms, a cycloalkyl radical having 4 to 6 carbon atoms or a benzyl radical,
or $R_1$ and $R_2$ taken together form a radical —CO—, and n is 0 or 1,
with the proviso that when n is 0 and $R_1$ is —$CO_2R'_2$, $R_2$ and $R'_2$ do not simultaneously represent the radical $CH_3$,
and the isomers of the compounds of formula (I) and mixtures thereof.

4 Claims, No Drawings

1,8-DIHYDROXY-9-ANTHRONES DERIVATIVES SUBSTITUTED IN THE 10-POSITION BY AN UNSATURATED RADICAL USED IN HUMAN MEDICINE

This application is a divisional application of Ser. No. 346,893, filed Feb. 8, 1982, now U.S. Pat. No. 4,464,301.

The present invention relates to novel derivatives of novel 1,8-dihydroxy-9-anthrones substituted in the 10-position by an unsaturated radical and their utilization in human and veterinary medicine and particularly in the treatment of psoriasis as well as in cosmetic.

These 1,8-dihydroxy-9-anthrones substituted in the 10-position by an unsaturated radical may be represented as compounds of the general formula:

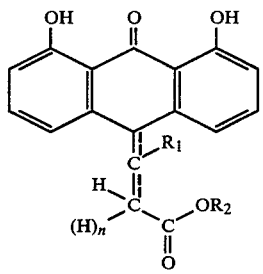

wherein:
$R_1$ represents a hydrogen atom or a $-CO_2R'_2$ radical,
$R_2$ and $R'_2$, identical or different, represent a hydrogen atom, a linear or branched chain alkyl radical having 1 to 6 carbon atoms, a cycloalkyl radical having 4 to 6 carbon atoms or a benzyl radical,
or $R_1$ and $R_2$ taken together form a radical $-CO-$, and
n is 0 or 1,
with the proviso that when n is 0 and $R_1$ is $-CO_2R'_2$, $R_2$ and $R'_2$ do not simultaneously represent the radical $CH_3$,
and the isomers of the compounds of formula (I) and mixtures thereof, Among the linear or branched chain alkyl radicals having 1 to 6 carbon atoms within the definition of $R_2$ and $R'_2$ the following radicals can be cited: methyl, ethyl, propyl, isopropyl, butyl, isobutyl, tertiary butyl, pentyl, and hexyl.

Among the cycloalkyl radicals within the definition of $R_2$ and $R'_2$ the following can be cited: cyclobutyl, cyclopentyl, and cyclohexyl.

According to a first object, the compounds according to the invention have the general formula:

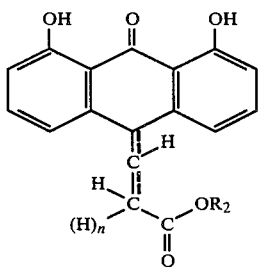

wherein
$R_2$ represents a hydrogen atom, a linear or branched chain alkyl radical having 1 to 6 carbon atoms, a cycloalkyl radical having 4 to 6 carbon atoms or a benzyl radical, and
n is 0 or 1.

According to a second object, the compounds of the invention have the general formula:

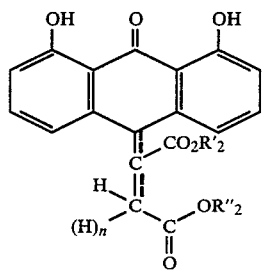

wherein
$R'_2$ represents a hydrogen atom, a linear or branched chain alkyl radical having 1 to 6 carbon atoms, a cycloalkyl radical having 4 to 6 carbon atoms, or a benzyl radical,
$R''_2$ represents a hydrogen atom, a linear or branched chain alkyl radical having 2 to 6 carbon atoms, a cycloalkyl radical having 4 to 6 carbon atoms, or a benzyl radical, and
n is 0 or 1.

According to the general formula (I), the compounds of the invention can be represented by the two following formulas (II) or (III) or in the form of their mixture.

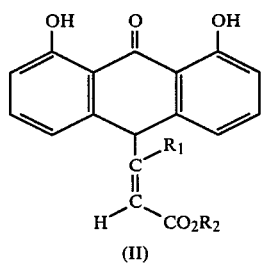

and/or

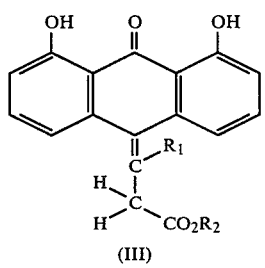

In these formulas the radicals $R_1$ and $R_2$ have the same meaning as above.

Some methods of preparation which are described herein below are susceptible of directing formation of a compound of structure (II) or of a compound of structure (III).

Other methods of synthesis lead to the preponderant formation of a compound (II) or (III) contaminated by one or the other of the isomers.

Purification methods are susceptible in that latter case to isolate one or the other compound in the pure state.

Among the compounds of the formula (II) there can in particular be cited those given in Table A.

TABLE A

| Compound No. | | $R_1$ | $R_2$ |
|---|---|---|---|
| 1 | 10-(1,8-dihydroxy-9-anthrone)-yl maleic anhydride | —CO— | |
| 2 | 10-(1,8-dihydroxy-9-anthrone)-yl maleic acid | —COOH | H |
| 3 | diethyl 10-(1,8-dihydroxy-9-anthrone)-yl maleate | —COOC$_2$H$_5$ | —C$_2$H$_5$ |
| 4 | dipropyl 10-(1,8-dihydroxy-9-anthrone)-yl maleate | —COOC$_3$H$_7$ | —C$_3$H$_7$ |
| 5 | diisopropyl 10-(1,8-dihydroxy-9-anthrone)-yl maleate | —COO—isoC$_3$H$_7$ | -isoC$_3$H$_7$ |
| 6 | dibutyl 10-(1,8-dihydroxy-9-anthrone)-yl maleate | —COOC$_4$H$_9$ | —C$_4$H$_9$ |
| 7 | dipentyl 10-(1,8-dihydroxy-9-anthrone)-yl maleate | —COOC$_5$H$_{11}$ | —C$_2$H$_{11}$ |
| 8 | dihexyl 10-(1,8-dihydroxy-9-anthrone)-yl maleate | —COOC$_6$H$_{13}$ | —C$_6$H$_{13}$ |
| 9 | dicyclobutyl 10-(1,8-dihydroxy-9-anthrone)-yl maleate | —COOC$_4$H$_7$ | —C$_7$H$_7$ |
| 10 | dicyclopentyl 10-(1,8-dihydroxy-9-anthrone)-yl maleate | —COOC$_5$H$_9$ | —C$_5$H$_9$ |
| 11 | dicyclohexyl 10-(1,8-dihydroxy-9-anthrone)-yl maleate | —COOC$_6$H$_{11}$ | —C$_6$H$_{11}$ |
| 12 | dibenzyl 10-(1,8-dihydroxy-9-anthrone)-yl maleate | —COOCH$_2$C$_6$H$_5$ | —CH$_2$C$_6$H$_5$ |
| 13 | methyl pentyl 10-(1,8-dihydroxy-9-anthrone)-yl maleate | —COOCH$_3$ | —C$_5$H$_{11}$ |
| 14 | methyl hexyl 10-(1,8-dihydroxy-9-anthrone)-yl maleate | —COOCH$_3$ | —C$_6$H$_{13}$ |
| 15 | ethyl butyl 10-(1,8-dihydroxy-9-anthrone)-yl maleate | —COOC$_2$H$_5$ | —C$_4$H$_9$ |
| 16 | ethyl pentyl 10-(1,8-dihydroxy-9-anthrone)-yl maleate | —COOC$_2$H$_5$ | —C$_5$H$_{11}$ |
| 17 | ethyl hyexyl 10-(1,8-dihydroxy-9-anthrone)-yl maleate | —COOC$_2$H$_5$ | —C$_6$H$_{13}$ |
| 18 | propyl pentyl 10-(1,8-dihydroxy-9-anthrone)-yl maleate | —COOC$_3$H$_7$ | —C$_5$H$_{11}$ |
| 19 | isopropyl butyl 10-(1,8-dihydroxy-9-anthrone)-yl maleate | —COO—isoC$_3$H$_7$ | —C$_4$H$_9$ |
| 20 | methyl 10-(1,8-dihydroxy-9-anthrone)-yl maleate | —COOH | —CH$_3$ |
| 21 | ethyl 10-(1,8-dihydroxy-9-anthrone)-yl maleate | —COOH | —C$_2$H$_5$ |
| 22 | propyl 10-(1,8-dihydroxy-9-anthrone)-yl maleate | —COOH | —C$_3$H$_7$ |
| 23 | butyl 10-(1,8-dihydroxy-9-anthrone)-yl maleate | —COOH | —C$_4$H$_9$ |
| 24 | pentyl 10-(1,8-dihydroxy-9-anthrone)-yl maleate | —COOH | —C$_5$H$_{11}$ |
| 25 | hexyl 10-(1,8-dihydroxy-9-anthrone)-yl maleate | —COOH | —C$_6$H$_{13}$ |

Among the compounds of formula (III) there can in particular be cited those given in Table B.

TABLE B

| Compound No. | | $R_1$ | $R_2$ |
|---|---|---|---|
| 26 | 3-[(1,8-dihydroxy-9-anthron)-10-ylidene] propionic acid | H | H |
| 27 | methyl 3-[(1,8-dihydroxy-9-anthron)-10-ylidene] propionate | H | —CH$_3$ |
| 28 | ethyl 3-[(1,8-dihydroxy-9-anthron)-10-ylidene] propionate | H | —C$_2$H$_5$ |
| 29 | propyl 3-[(1,8-dihydroxy-9-anthron)-10-ylidene] propionate | H | —C$_3$H$_7$ |
| 30 | butyl 3-[(1,8-dihydroxy-9-anthron)-10-ylidene] propionate | H | —C$_4$H$_9$ |
| 31 | pentyl 3-[(1,8-dihydroxy-9-anthron)-10-ylidene] propionate | H | —C$_5$H$_{11}$ |
| 32 | hexyl 3-[(1,8-dihydroxy-9-anthron)-10-ylidene] propionate | H | —C$_6$H$_{13}$ |
| 33 | cyclobutyl 3-[(1,8-dihydroxy-9-anthron)-10-ylidene]-propionate | H | —C$_4$H$_7$ |
| 34 | cyclopentyl 3-[(1,8-dihydroxy-9-anthron)-10-ylidene]-propionate | H | —C$_5$H$_9$ |
| 35 | cyclohexyl 3-[(1,8-dihydroxy-9-anthron)-10-ylidene]-propionate | H | —C$_6$H$_{11}$ |
| 36 | 3-[(1,8-dihydroxy-9-anthron)-10-ylidene]-succinic acid | —COOH | H |
| 37 | dimethyl 3-[(1,8-dihydroxy-9-anthron)-10-ylidene]-succinate | —COOCH$_3$ | —CH$_3$ |
| 38 | diethyl 3-[(1,8-dihydroxy-9-anthron)-10-ylidene]-succinate | —COOC$_2$H$_5$ | —C$_2$H$_5$ |
| 39 | dipropyl 3-[(1,8-dihydroxy-9-anthron)-10-ylidene]-succinate | —COOCC$_3$H$_7$ | —C$_3$H$_7$ |
| 40 | diisopropyl 3-[(1,8-dihydroxy-9-anthron)-10-ylidene]-succinate | —COO—isoC$_3$H$_7$ | -isoC$_3$H$_7$ |
| 41 | dibutyl 3-[(1,8-dihydroxy-9-anthron)-10-ylidene]-succinate | —COOC$_4$H$_9$ | —C$_4$H$_9$ |
| 42 | diisobutyl 3-[(1,8-dihydroxy-9-anthron)-10-ylidene]-succinate | —COO—isoC$_4$H$_9$ | -isoC$_4$H$_9$ |
| 43 | dipentyl 3-[(1,8-dihydroxy-9-anthron)-10-ylidene]-succinate | —COOC$_5$H$_{11}$ | —C$_5$H$_{11}$ |
| 44 | dihexyl 3-[(1,8-dihydroxy-9-anthron)-10-ylidene]-succinate | —COOC$_6$H$_{13}$ | —C$_6$H$_{13}$ |
| 45 | dicyclobutyl 3-[(1,8-dihydroxy-9-anthron)-10-ylidene]-succinate | —COOC$_4$H$_7$ | —C$_4$H$_7$ |
| 46 | dicyclopentyl 3-[(1,8-dihydroxy-9-anthron)-10-ylidene]-succinate | —COOC$_5$H$_9$ | —C$_5$H$_9$ |
| 47 | dicyclohexyl 3-[(1,8-dihydroxy-9-anthron)-10-ylidene]-succinate | —COOC$_6$H$_{11}$ | —C$_6$H$_{11}$ |
| 48 | 3-[(1,8-dihydroxy-9-anthron)-10-ylidene]-3-methoxycarbonyl propionic acid | —COOCH$_3$ | H |
| 49 | 3-[(1,8-dihydroxy-9-anthron)-10-ylidene]-3- | —COOC$_2$H$_5$ | H |

TABLE B-continued

| Compound No. | | $R_1$ | $R_2$ |
|---|---|---|---|
| | ethoxycarbonyl propionic acid | | |
| 50 | 3-[(1,8-dihydroxy-9-anthron)-10-ylidene]-3-propyloxycarbonyl propionic acid | —COOC$_3$H$_7$ | H |
| 51 | 3-[(1,8-dihydroxy-9-anthron)-10-ylidene]-3-butyloxycarbonyl propionic acid | —COOC$_4$H$_9$ | H |
| 52 | 3-[(1,8-dihydroxy-9-anthron)-10-ylidene]-3-pentyloxy propionic acid | —COOC$_5$H$_{11}$ | H |
| 53 | 3-[(1,8-dihydroxy-9-anthron)-10-ylidene]-3-hexyloxycarbonyl propionic acid. | —COOC$_6$H$_{13}$ | H |

The compounds according to the invention can be prepared according to a first synthetic method by condensing an unsaturated ethylenic or acetylenic reagent with 1,8-dihydroxy-9-anthrone (anthralin).

This synthetic method may be represented by the following reaction scheme:

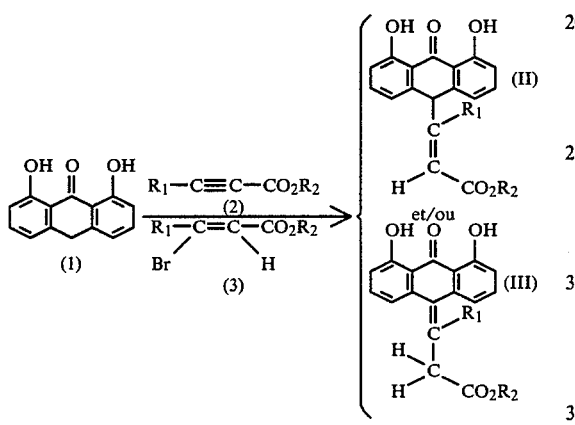

If the compound of formula (2) is an alkyl propriolate ($R_1$=H) the reaction is more particularly orientated to the formation of a compound of formula (III). By contrast, if the compound of formula (2) is an alkyl acetylene dicarboxylate ($R_1$=CO$_2$R'$_2$), the reaction is more especially oriented to the formation of a compound of formula (II).

The reaction in presence of the acetylenic compounds (2) is generally conducted in an organic solvent medium such as dimethylformamide, pyridine or chloroform.

If chloroform is used as a solvent, the reaction is carried out in presence of a basic catalyst, preferably in presence of 4-dimethylaminopyridine.

The reaction is preferably carried out in an inert atmosphere and protected from atmospheric moisture and from light. The reaction temperature depends on the nature of the solvent used; thus the reaction is carried out at 0° C. with pyridine, but at room temperature with dimethylformamide and at reflux with chloroform.

The reaction progress is followed by thin layer chromotography in order to determine the progressive disappearance of 1,8-dihydroxy-9-anthrone.

The reaction time may be varied between several minutes to several hours in the case of chloroform.

At the end of the reaction, the product is isolated either by precipitation with a co-solvent or by usual treatment, i.e. by washing the organic phase and then by concentrating it. The mixture obtained is then fractionated by column chromotagraphy on silica gel.

The compounds according to the invention may also be obtained by reacting an halogenated ethylenic derivative and more particularly a compound of the formula (3) with 1,8-dihydrox-9-anthrone under the same conditions which have been described above for the acetylenic reagents.

This method of synthesis leads especially to the compounds of formula (II).

The compounds of formula (II) are, according to this invention, preferably obtained by thermolysis of adducts of 1,8-dihydroxy-9-anthrones described in our copending application Ser. No. 312,640 filed Oct. 19, 1981. This method of synthesis can be represented by the following reaction scheme:

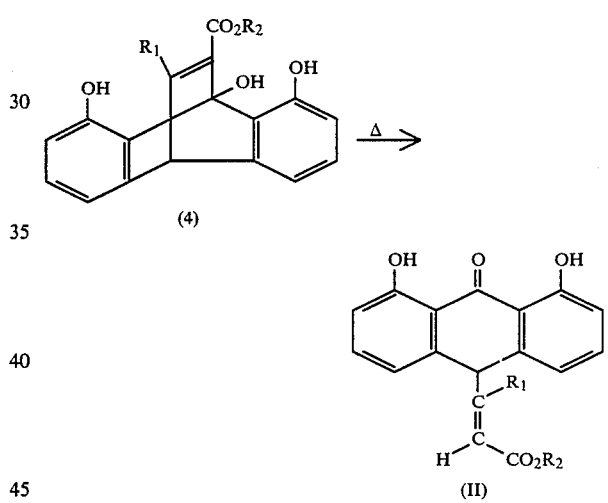

This method of synthesis involves preparing a suspension of an adduct of formula (4) wherein the radical $R_1$ represents preferably the radical —CO$_2$R'$_2$, i.e. a dialkyl 9,10-dihydro-1,8,9-trihydroxy-9,10-anthracene-α,β-endomaleate, in a solvent of high boiling point such as for instance ortho-dichlorobenzene or decalin.

The mixture obtained is maintained under an inert atmosphere and protected from light at the boiling point of the solvent for several hours.

After cooling the reaction mixture, the unreacted starting material is removed by filtration and the product obtained is isolated either by precipitation with an appropriate solvent or by column chromatography on silica gel.

The adducts of formula (4) are prepared by reacting, in an inert atmosphere and protected from light and moisture, 1,8-dihydroxy-9-anthrone in an appropriate organic solvent such as tetrahydrofuran with an alkyl acetylenedicarboxylate. The presence of a catalyst can be desirable.

The compounds of formula (III), in which $R_2$ and $R'_2$ are different, are generally obtained by a transesterification reaction by treating the compounds wherein $R_2=R'_2$ with an alcohol in acidic medium.

The object of the present invention is likewise the utilization of the compounds according to the invention in human or veterinary medicine and particularly for the treatment of psoriasis or acne, as well as in cosmetic.

According to the invention the compounds as defined hereinabove are incorporated into pharmaceutical or cosmetic compositions in a concentration generally comprised between 0.01 to 5% and preferably between 0.1 and 3% in an appropriate pharmaceutical or cosmetic vehicle.

Cutaneous psoriasis is essentially manifested by the appearance of dry, whitish or nacreous scales, especially on the knees, elbows, sacrum, soles of the feet, palms of the hand, chest and face and likewise on hairy hide.

The various tests conducted have shown that the compounds according to the invention have a good activity when they are incorporated in various pharmaceutical vehicles for systemic and particularly percutaneous route of administration.

Several examples will now be given, by way of illustration and without any limitative character, of the preparation of the compounds according to the invention.

EXAMPLE 1

10-(1,8-dihydroxy-9-anthronyl)maleic anhydride (No. 1)

In a first step 15 g of anthralin are dissolved at 80° C. in 50 ml of dimethylformamide, freshly distilled, under an argon atmosphere and protected from light. After return to room temperature a slight excess of bromomaleic anhydride, (7 ml) is added in one batch under stirring.

After two hours all of the anthralin has been transformed; 200 ml of dichloromethane is then added and the mixture thus obtained is washed repeatedly with water. The organic layer is dried over sodium sulfate, then evaporated to dryness at reduced pressure.

The solid obtained is washed with ether, then dissolved in methylene chloride and treated with animal charcoal.

The anhydride obtained is finally recrystallized in methylene chloride; the yellow orange crystals have a melting point of 215° C.

Analysis: $C_{18}H_{10}O_6$. Calc: C: 67.09; H: 3.13; O: 29.79. Found: C: 67.29; H: 3.41; O: 29.60.

EXAMPLE 2

10-(1,8-dihydroxy-9-anthrone)-yl maleic acid (No. 2)

A solution of 2 g of 10-(1,8-dihydroxy-9-anthrony)-maleic anhydride, obtained according to Example 1, in a mixture of 85 ml of acetic acid and 15 ml of water is maintained at reflux for one hour in an inert atmosphere and protected from light. The solution is then evaporated at reduced pressure.

The solid thus obtained is stirred for one hour in 50 ml of methylene chloride, then filtered and dried. 10-(1,8-dihydroxy-9-anthrone)-yl maleic acid is thus obtained in the form of a yellow orange powder having a melting point of 240° C.

Analysis: $C_{18}H_{12}O_7$. Calc: C: 63.53; H: 3.55; O: 32.91. Found: C: 63.45; H: 3.71; O: 33.11.

EXAMPLE 3

Diethyl 10-(1,8-dihydroxy-9-anthrone)-yl maleate (No. 3)

To a stirred suspension of 5 g of anthralin in 250 ml of chloroform, in an inert atmosphere, and protected from moisture and light, 5.63 g of ethyl acetylenedicarboxylate and then 300 mg of 4-dimethylaminopyridine are added. The mixture is maintained at the boiling point of chloroform during 90 minutes after which time all the anthralin has reacted. The solvent is then evaporated under reduced pressure and the residue is taken up in a minimum amount of benzene. The benzene phase is then deposited on a silica gel chromatography column. The desired product is eluted with benzene and then, after concentration of the elution phases, the residue is recrystalized from ethanol.

The yellow crystals thus obtained have a melting point of 122° C.

Analysis: $C_{22}H_{20}O_7$. Calc: C: 66.66; H: 5.08; O: 28.25. Found: C: 66.83; H: 5.14; O: 28.20.

EXAMPLE 4

Diisopropyl 10-(1,8-dihydroxy-9-anthrone)-yl maleate (No. 5)

(1) To a suspension of 11.3 g of anthralin in 150 ml of anhydrous THF, placed under an inert atmosphere and protected from atmospheric moisture and light, there are added 15 g of diisopropyl acetylenedicarboxylate, then 4 ml of an 0.5% methanol solution of lithium methylate. The reaction mixture is brought to the boiling point of THF during two hours, then concentrated under reduced pressure. The dark red residue is dissolved in a minimum amount of toluene. The toluene phase is deposited on a silica gel chromatography column.

The diisopropyl 9,10-dihydro-1,8,9-trihydroxy-9,10-anthracene-α,β-endomaleate is eluted with chloroform, then recrystallized form a methylene chloride/hexane mixture after concentration of the elution phases. After draining and drying, there are obtained 10 g of white crystals with melting point 203° C.

Analysis: $C_{24}H_{24}O_7$. Calc: C: 67.91; H: 5.70; O: 26.39. Found: C: 68.15; H: 5.90; O: 26.47.

(2) A solution of 4 g of diisopropyl 9,10-dihydro-1,8,9-trihydroxy-9,10-anthracene-α,β-endomaleate in 15 ml of ortho-dichlorobenzene, stirred under an argon atmosphere and protected from light, is brought at reflux temperature for 40 hours. The reaction mixture is then filtered. To the filtrate 100 ml of hexane is added and the resulting precipitate is filtered and dried.

The product obtained is then dissolved in the minimum amount of toluene and deposited on a silica gel chromatography column. The expected product is eluted with toluene. After concentration of the eluates, the recrystalization from a mixture of hexane and methylene chloride (9:1) gives rise to yellow needles having a melting point of 132° C.

Analysis: $C_{14}H_{24}O_7$. Calc: C: 67.91; H: 5.70; O: 26.39. Found: C: 68.01; H: 5.66; O: 26.36.

EXAMPLE 5

Dibutyl 10-(1,8-dihydroxy-9-anthrone)-yl maleate (No. 6)

(1) To a suspension of 3.40 g of anthralin in 40 ml of anhydrous tetrahydrofuran, placed under an argon atmosphere and protected from atmospheric moisture and light, there are successively added 1 ml of a 0.5% methanolic solution of lithium methylate, then 5 g of freshly distilled dibutyl acetylenedicarboxylate. The reaction mixture is then brought to the boiling point of tetrahydrofuran during two hours. It is then concentrated under reduced pressure. The residual oil obtained is diluted with 30 ml of benzene, and the solution is then deposited directly onto a silica gel column. The expected product is eluted with chloroform. After concentration of the chloroform phases, the solid is crystallized once from cyclohexane and then from a hexane/benzene mixture. The white crystals of dibutyl 9,10-dihydro-1,8,9-trihydrox-9,10-anthracene-α,β-endomaleate thus isolated melt at 148° C.

Analysis: $C_{26}H_{28}O_7$. Calc: C: 69.01; H: 6.24; O: 24.75. Found: C: 68.86; H: 6.26; O: 24.85.

(2) A solution of 2 g of dibutyl 9,10-dihydro-1,8,9-trihydroxy-9,10-anthracene-α,β-endomaleate in 7 ml of freshly distilled ortho-dichlorobenzene is brought at the boiling point of ortho-dichlorobenzene for 24 hours, the solution being maintained in an inert atmosphere and protected from light.

After cooling, the mixture is diluted with hexane and the unreacted starting material precipitates. After filtration, the filtrate is concentrated under reduced pressure and the solution obtained is deposited on a silica gel column. The expected product is eluted with benzene. After concentration of the benzene phase, a yellow solid is obtained with a melting point of 56° C.

Analysis: $C_{26}H_{28}O_7$. Calc: C: 69.01; H: 6.24; O: 24.75. Found: C: 68.96; H: 6.19; O: 24.48.

EXAMPLE 6

Dicyclohexyl 10-(1,8-dihydroxy-9-anthrone)-yl maleate (No. 11)

(1) To a suspension of 11.3 g of anthralin in 150 ml of anhydrous tetrahydrofuran, protected from atmospheric moisture and light and placed under an inert atmosphere, there are added 20.38 g of dicyclohexyl acetylenedicarboxylate and 3.5 ml of a 0.5% methanolic solution of lithium methylate. The reaction mixture is maintained at the boiling point of tetrahydrofuran for one hour. After concentration under reduced pressure, the product obtained is dissolved in a minimum of toluene and deposited on a silica gel chromatography column. The dicyclohexyl 9,10-dihydro-1,8,9-trihydroxy-9,10-anthracene-α,β-endomaleate is eluted with a 4:1 mixture of toluene/ethyl acetate, then crystallized from a mixture of toluene and hexane and finally washed with methylene chloride. After drying, there are thus obtained 16 g of white crystals with a melting point of 230° C.

Analysis: $C_{30}H_{32}O_7$. Calc: C: 71.41; H: 6.39. Found: C: 71.63; H: 6.48.

(2) A solution of 1.8 g of the above product in 7 ml of ortho-dichlorobenzene is maintained for 12 hours in an inert atmosphere and protected from light at the boiling temperature of the solvent. After cooling the solution is diluted with 100 ml of cyclohexane.

A portion of the starting material precipitates and is filtered off.

The filtrate is then concentrated and deposited on a silica gel column. The product is eluted with benzene. After evaporation of the benzene phases, a yellow solid is obtained having a melting point of 178° C.

Analysis: $C_{30}H_{32}O_7$. Calc: C: 71.41; H: 6.39. Found: C: 71.54; H: 6.42.

EXAMPLE 7

Dibenzyl 10-(1,8-dihydroxy-9-anthrone)-yl maleate (No. 12)

A suspension of 2.1 g of anthralin in 4 ml of benzyl acetylenedicarboxylate is brought to a temperature of 140° C. in an inert atmosphere, then maintained for one hour at 120° C. after addition of several crystals of potassium carbonate. After cooling, the reaction mixture is dissolved in a minimum of chloroform and the chloroform phase is deposited on a silica gel column.

The product is eluted with benzene; after concentration of the eluates, a yellow solid is obtained having a melting point of 84° C.

Analysis: $C_{32}H_{24}O_7$. Calc: C: 73.84; H: 4.65; O: 21.51. Found: C: 73.67; H: 4.68; O: 21.41.

EXAMPLE 8

Methyl 3-[(1,8-dihydroxy-9-anthron)10-ylidene]-propionate (No. 27)

To a solution of anthralin (5 g) in 300 ml of chloroform under an argon atmosphere and protected from light, 4 ml of methyl propiolate and 300 mg of 4-dimethylaminopyridine are added under stirring in one batch.

The solution is then maintained at reflux for 20 hours. After cooling and washing with acidified water, the chloroform phase is decanted, dried over sodium sulfate and then concentrated. The residue is taken up in the minimum amount of benzene and the benzene phase is deposited on a silica gel column. The expected product is eluted with chloroform. After concentration of the eluates, the solid obtained is recrystalized from acetone. After drying under reduced pressure the yellow crystals have a melting point 172° C.

Analysis: $C_{18}H_{14}O_5$. Calc: C: 69.67; H: 4.55; O: 25.78. Found: C: 69.60; H: 4.62; O: 25.83.

EXAMPLE 9

Ethyl 3-[(1,8-dihydroxy-9-anthron)10-ylidene]-propionate (No. 28)

To a stirred solution of anthralin (5 g) in 300 ml of chloroform under an atmosphere of argon and protected from light, 3 ml of ethyl propriolate and 200 mg of 4-dimethylaminopyridine are added in one batch.

The mixture is maintained for 36 hours at reflux. After cooling, the mixture is washed with acidified water. The chloroform phase is decanted, dried over sodium sulfate and then evaporated under reduced pressure. The residue is dissolved in the minimum amount of toluene and the toluene phase is deposited on a silica gel column. The expected product is eluted with toluene. The solid obtained after concentration of the eluates is recrystalized from acetone. The yellow crystals thus isolated have a melting point of 145° C. after drying.

Analysis: $C_{19}H_{16}O_5$. Calc: C: 70.36; H: 4.97; O: 24.66. Found: C: 70.45; H: 4.99; O: 24.62.

EXAMPLE 10

Pentyl 3-[(1,8-dihydroxy-9-anthron)10-ylidene]-propionate (No. 31)

A solution of 1 g of methyl (1,8-dihydroxy-9-anthron-10-ylidene)-3-propionate obtained, according to Example 8, in 25 ml of pentanol containing 2 drops of concentrated sulfuric acid is maintained at a temperature of 130° C. for one hour in an inert atmosphere and protected from light. The mixture is then concentrated under reduced pressure, the residue is taken up in toluene and the toluene phases are washed with water, dried over sodium sulfate and finally deposited on a silica gel column. The product is then eluted with methylene chloride. After concentration of the eluates 0.75 g of a yellow orange liquid is obtained.

Analysis: $C_{22}H_{22}O_5$. Calc: C: 72.12; H: 6.05; O: 21.83. Found: C: 72.11; H: 6.09; O: 21.78.

EXAMPLE 11

Cyclohexyl 3-[(1,8-dihydroxy-9-anthron)10-ylidene]-propionate (No. 35)

A solution of 1 g of methyl 3-[(1,8-dihydroxy-9-anthron)10-ylidene]-propionate, obtained according to Example 8, in 25 ml of cyclohexanol containing 2 drops of concentrated sulfic acid is maintained at a temperature of 130° for 5 hours in an inert atmosphere and protected from light. The reaction mixture is then treated as in Example 9 above. After purification on a silica gel column, 0.7 g of the product is obtained which is then recrystalized from hexane. The yellow orange crystals are filtered and dried under reduced pressure. Melting point: 70° C.

Analysis: $C_{23}H_{22}O_5$. Calc: C: 73.00; H: 5.86; O: 21.14. Found: C: 72.92; H: 5.89; O: 21.06.

EXAMPLE 12

Dimethyl 3-[(1,8-dihydroxy-9-anthron)10-ylidene]-succinate (No. 37)

To a solution of anthralin (10 g) in 500 ml of chloroform under an inert atmosphere and protected from light, 6.5 ml of methyl acetylenedicarboxylate and 200 mg of 4-dimethylaminopyridine are added in one batch. The reaction mixture is then maintained for 4 hours at reflux. After cooling and washing with water, the chloroform phase is dried over sodium sulfate and then concentrated under reduced pressure. The residue obtained is dissolved in a minimum of benzene and the benzene phase is deposited on a silica gel column.

The expected product is eluted with chloroform. After concentration of the eluates, the solid obtained is recrystalized from a mixture of benzene and ethanol. The yellow crystals are filtered and dried under reduced pressure. Melting point: 152° C.

Analysis: $C_{20}H_{16}O_7$. Calc: C: 65.22; H: 4.38; O: 30.41. Found: C: 65.15; H: 4.40; O: 30.31.

Regarding the treatment of psoriasis, a composition containing an active compound of the present invention is applied topically to the affected area of the skin. Generally, the compositions are applied in a thickened form with the aid of a thickening agent such as petrolatum U.S.P.

Examples of anti-psoriasis composition embodied within the scope of the present invention are as follows:

| | |
|---|---|
| (1) dicyclohexyl 10-(1,8-dihydroxy-9-anthrone)-yl maleate | 2 g |
| Petrolatum U.S.P. | 98 g |
| (2) dibenzyl 10-(1,8-dihydroxy-9-anthrone)-yl maleate | 2 g |
| Hydrocortisone | 1 g |
| Petrolatum U.S.P. | 97 g |
| (3) pentyl 3-[(1,8-dihydroxy-9-anthron)-10-ylidene]-propionate | 2 g |
| salicylic acid | 2 g |
| Petrolatum U.S.P. | 96 g |
| (4) methyl 3-[(1,8-dihydroxy-9-anthron)-10-ylidene]-propionate | 0.5 g |
| salicylic acid | 2 g |
| Petrolatum U.S.P. | 97.5 g |
| (5) dimethyl 3-[(1,8-dihydroxy-9-anthron)-10-ylidene]-succinate | 1 g |
| Hard paraffin | 5 g |
| Starch | 50 g |
| Soft white paraffin | 44 g |

As regards examples 1–4 above, the active compound is added to Petrolatum under stirring at 60° C. and, if desired, the salicylic acid or the hydrocortisone. After cooling at room temperature, the resulting suspension is refined by passing it to roller mill.

By applying the above compositions once daily during three weeks, excellent results are obtained on the psoriasis areas of the skin. The efficiency is superior or equal to compositions containing anthralin but with no primary irritation and without staining of the skin.

What is claimed is:

1. A composition to be topically applied to the skin, which contains in a paraffin vehicle suitable for application to the skin, 0.01 to 5% by weight of a compound of the following formula:

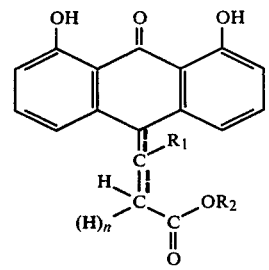

wherein
$R_1$ represents hydrogen or $CO_2R'_2$,
$R_2$ and $R'_2$, identical or different, represent hydrogen, linear or branched chain alkyl radical of 1 to 6 carbon atoms, cycloalkyl of 4 to 6 carbon atoms or benzyl,
or $R_1$ and $R_2$ taken together form a —CO—, and
n is 0 or 1,
and mixtures thereof.

2. A composition to be topically applied to the skin, which contains in a vehicle suitable for application to the skin, 0.01 to 5% by weight of a compound of the formula:

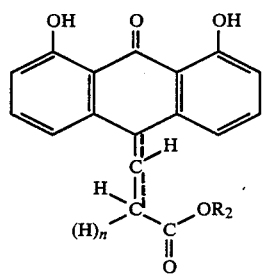

wherein:
R₂ represents hydrogen, linear or branched alkyl of 1 to 6 carbon atoms, cycloalkyl of 4 to 6 carbon atoms or benzyl, and
n is 0 or 1,
and mixtures thereof.

3. A method for the treatment of psoriasis or acne which comprises topically applying to the affected area of the skin an effective amount of the composition of claim 2.

4. A method for treatment of psoriasis or acne which comprises topically applying to the affected area of the skin an effective amount of the compound of the formula:

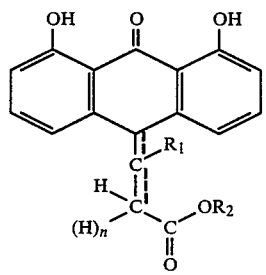

wherein
R₁ represents hydrogen or CO₂R'₂,
R₂ and R'₂, identical or different, represent hydrogen, linear or branched chain alkyl radical of 1 to 6 carbon atoms, cycloalkyl of 4 to 6 carbon atoms or benzyl,
or R₁ and R₂ taken together form a —CO—, and
n is 0 or 1,
and mixtures thereof.

* * * * *

UNITED STATES PATENT AND TRADEMARK OFFICE
CERTIFICATE OF CORRECTION

PATENT NO. : 4,558,069
DATED : December 10, 1985
INVENTOR(S) : SHROOT et al.

It is certified that error appears in the above-identified patent and that said Letters Patent is hereby corrected as shown below:

On the cover page of the patent, above item [51], insert

--Foreign Priority Data
French Application No. 81 02572, filed February 10, 1981.--

Signed and Sealed this

Twenty-third Day of September 1986

[SEAL]

Attest:

DONALD J. QUIGG

Attesting Officer     Commissioner of Patents and Trademarks